(12) United States Patent
Rubin

(10) Patent No.: US 6,407,071 B1
(45) Date of Patent: Jun. 18, 2002

(54) METHOD AND COMPOSITION FOR TREATING MALIGNANT CELLS

(75) Inventor: David Rubin, San Diego, CA (US)

(73) Assignee: Co-Enzyme Technology Ltd., San Diego, CA (US)

( * ) Notice: Subject to any disclaimer, the term of this patent is extended or adjusted under 35 U.S.C. 154(b) by 0 days.

(21) Appl. No.: 09/694,679

(22) Filed: Oct. 24, 2000

Related U.S. Application Data

(63) Continuation-in-part of application No. 09/090,386, filed on Jun. 4, 1998, now abandoned.

(51) Int. Cl.$^7$ .................................................. A61K 31/70
(52) U.S. Cl. ........................... 514/23; 514/25; 514/693; 514/699
(58) Field of Search ............................ 514/23, 25, 693, 514/699

(56) References Cited

U.S. PATENT DOCUMENTS 4,882,314 A * 11/1989 Takeuchi et al. ............... 514/23
5,476,842 A * 12/1995 Rubin ........................ 514/25

* cited by examiner

*Primary Examiner*—Elli Peselev
(74) *Attorney, Agent, or Firm*—Browdy and Neimark

(57) ABSTRACT

A composition for treating tumors comprising a combination of at least one oxidizing agent and at least one aldehyde or precursor thereof, which aldehyde forms an insoluble thiazoline with cysteine. Optionally a compound which inhibits glutathione-s-transferase is included.

21 Claims, No Drawings

METHOD AND COMPOSITION FOR TREATING MALIGNANT CELLS

CROSS-REFERENCE TO RELATED APPLICATIONS

The present application is a continuation in part of Ser. No. 09/090,386 filed Jun. 4, 1998, now abandoned, the entire contents of which are hereby incorporated by reference.

FIELD OF THE INVENTION

The present invention is directed to a method and composition for treating malignant cells.

BACKGROUND OF THE INVENTION

Control of cell growth is one of the most important aspects of an animal's physiology. The cells of an adult must divide frequently enough to allow tissues to remain in a steady state, and division must be stimulated at wounds or when special requirements are placed on the tissues. There must be many circulating cell-specific factors that signal individual cell types whether to divide or not. However, uninhibited cell growth results in malignant tumors.

One of the greatest problems associated with treatment of cancers is delivery of a cytotoxic agent directly to the tumor or cancer cells without affecting normal cells of the body. Although it was hoped that monoclonal antibodies could be used as delivery agents for cytotoxic drugs to treat cancers and to inhibit metastasis of existing cancers, monoclonal antibodies have not lived up to their promise. One reason for this is that there is a very high density of receptors on the surface of cancer cells. Since monoclonal antibodies are relatively large compounds, it is impossible to provide sufficient amounts of monoclonal antibodies at the cell surface to effectively destroy the cells. In other words, the monoclonal antibodies are so large that only a very few can be present at the surface of a cell at any one time.

There have been many reports in the literature relating to the general concept of providing direct transport of an agent which is toxic to tumor cells directly to tumors having β-glucuronidase activity by conjugating the agent with glucuronic acid. Among such reports are Von Ardenne et al., *Agressologie*, 176(5):261–264 (1976); East German Patent No. 122,386; German Offenlegungsschrift 22 12 014; Sweeney et al., *Cancer Research*, 31:477–478 (1971); Baba et al., *Gann*, 69:283–284; and Ball, *Biochem. Pharm.*, 23:3171–3177 (1974).

Von Ardenne et al. suggest many types of aglycones which may be conjugated to glucuronic acid and will be active at the tumor site. These include, broadly, alkylating groups, antimetabolites, cytotoxins, membrane-active (lytic) groups, glycolysis stimulators, respiration inhibitors, inorganic and organic acids, and cell cycle stoppers. East German Patent No. 122,386 also suggests many such combinations, including 5-fluorourcil-glucuronide, aniline mustard-glucuronide, and many others. German offenlegungsschrift also mentions a large number of glucuronides. Sweeney et al. disclose the anti-tumor activity of mycophenolic acid-β-glucuronides. Baba et al. note the antitumor activity of 5-fluorouracil-O-β-D-glucuronide, and Ball discloses the anti-tumor activity of p-hydroxyaniline mustard glucuronide.

Kneen, in European Patent application 054,924, discloses phenyl ether compounds which can be used to make tumors more sensitive to radiotherapy.

Rubin, in U.S. Pat. Nos. 4,337,760 and 4,481,195, discloses methods for treating tumors having high β-glucuronidase activity with glucuronides with aglycones toxic to the tumor cells while protecting the rest of the body by first administering an alkalizing agent in an amount sufficient to maintain the pH level of non-tumor tissues at approximately 7.5 during the glucuronide treatment to inactivate β-glucuronidase activity in the rest of the body. Thus, the toxic agent is released only at the cancer cells, rather than to all of the healthy cells of the body, since the aglycone is only released at the site of the cancer. Tumors having high glucuronidase activity can be identified by assaying tumor cells obtained in a biopsy for β-glucuronidase activity, or by administering a glucuronide whose aglycone has been labelled with a radioactive isotope. If, upon a full body scan, it is found that the radioisotope has accumulated at any specific areas of the body, this will indicate not only the location of the tumor but the fact that the tumor has sufficient β-glucuronidase activity to deconjugate the glucuronide.

Rubin, in U.S. Pat. Nos. 5,649,737 and 5,476,842 discloses a variety of other compositions and methods of treating cancer cells using the high β-glucuronidase activity of many malignant cells. All of these patents are hereby incorporated in their entirety by reference.

Para-methoxy phenol, or 4-hydroxy anisole, has been used for treating melanoma because the only cells in vertebrates that contain tyrosinase are melanocytes. 4-Hydroxyanisole inhibits DNA synthesis, but by itself shows little toxicity. However, 4-hydroxyanisole is oxidized by tyrosinase to form highly cytotoxic products, and consequently, 4-hydroxyanisole is preferentially toxic to those melanoma cells that contain the enzyme tyrosinase [Riley, *Phils. Trans. R. Soc. (Biol.)*, 311: 679, (1985)]. Morgan et al., in *Clinical Oncology*, 7:227–231, (1981), also noted that 4-hydroxyanisole, which is oxidized by tyrosinase, gives rise to cytotoxic oxidation products. The specific melanocytotoxic action of this agent is of particular interest because of its use in treatment of malignant melanoma. It was found that localized malignant melanomas treated by intra-arterial infusion of 4-hydroxyanisole underwent regression, although intravenous administration of the drug was not therapeutically effective. The need to use the intra-arterial route of administration imposes certain limits on the use of 4-hydroxyanisole, since it is not always possible to perfuse the site occupied by a tumor. However, it is believed that, as an adjunct to the conventional treatment of primary melanoma in accessible sites, 4-hydroxyanisole infusion will reduce the dissemination of metastases.

Kanclerz et al., in *Br. J. Cancer*, 54:693–698 (1986), reported that animal studies on experimental melanomas have yielded variable results with respect to the therapeutic efficacy of phenolic depigmentation agents. The most active melanocytotoxic agent was found to be an analog of tyrosine, 4-hydroxyanisole. However, evidence for an antitumor effect of 4-hydroxyanisole on melanoma in vivo was found to be variable and not conclusive.

Unfortunately, intra-arterial infusion of 4-hydroxyanisole has serious clinical drawbacks, including difficulties in placing and maintaining the patency of intra-arterial catheters. Clogging and/or clotting frequently occurs, and, furthermore, 4-hydroxyanisole has a short half life in blood, only about nine minutes, following intra-arterial injection.

Saari, in U.S. Pat. No. 4,812,590, discloses that certain carbamates of 4-hydroxyanisole are suitable substitutes for 4-hydroxyanisole in melanoma treatment. These carbamates can be delivered by, for example, intravenous injection, and provide increased levels of 4-hydroxyanisole at the tumor site. This delivery of 4-hydroxyanisole is more convenient and is safer than many other methods for delivering 4-hydroxyanisole. However, because serum tyrosinase levels may be elevated in patients having tumors with high tyrosinase activity, the metabolic products of 4-hydroxyanisole may be present in locations other than the tumor site.

Pavel et al., in *Pigment Cells Research*, 2:241–241 (1999), reported an investigation of the human metabolism of 4-hydroxyanisole using urine samples from melanoma patients treated with 4-hydroxyanisole. The most important metabolite of 4-hydroxyanisole was found to be 3,4-dihydroxyanisole, although other metabolic products included 3-hydroxy-4-methoxyanisole and 4-hydroxyanisole-3-methoxyanisole, as well as quinone. These compounds were excreted predominantly as sulfates and glucuronides. Unfortunately, when tyrosinase oxidizes 4-hydroxyanisole in the body, the product, 4-methoxybenzoquinone, is extremely toxic. Because the 4-hydroxyanisole is not confined to the tumor site, and because the serum level of tyrosinase of patients suffering from tyrosinase-active tumors tends to be elevated, there is always the danger in administering 4-hydroxyanisole to such patients that an excess of the metabolic products of 4-hydroxyansole will be present in the blood, and thus exert a cytotoxic effect on cells other than tumor cells.

Chen et al. discovered that serum tyrosinase activity in many persons with metastatic diseases was significantly higher than this activity in healthy persons. Although the highest serum tyrosinase activity was observed in melanoma and breast carcinoma, there is measurable tyrosinase activity in a variety of other metastatic disease, including lung carcinoma, colon carcinoma, testicular carcinoma, hepatic carcinoma, pancreatic carcinoma, ovarian carcinoma, leukemia, bronchogenic carcinoma, prostate carcinoma, Hodgkin's disease, and rectal carcinoma, the tyrosinase activity of the foregoing carcinomas being listed in decreasing order.

In addition, serum melanin bands were demonstrated by polyacrylamide disc gel electrophoresis of serum tyrosinase followed by incubation of the gel with L-dopa at room temperature overweight to form melanin bands. The following types of metastatic disease exhibited serum melanin bands with this technique: mouth carcinoma, multiple myeloma, carcinoma of the stomach, carcinoma of the larynx, carcinoma of the cervix, carcinoma of the tonsil, lymphoma, lymphosarcoma, thyroid carcinoma, carcinoma of cecum, endometrial carcinoma polycythemia, thymoma, lymphadenopathy, and vertebral carcinoma.

Although the elevation of serum tyrosinase levels is explicable in some diseases, such as melanoma and breast carcinoma, the high tyrosinase content in melanoma and breast cancer increases the tyrosinase circulation level in the blood. Although it has not yet been determined if malignant disease causes a high level of serum tyrosinase, or if a high level of serum tyrosinase causes malignant disease, it has been postulated that serum immunoglobulins are involved as tyrosinase carriers. Whatever the involvement of tyrosinase in metastatic diseases, there is an elevated level of serum tyrosinase in the case of a great many metastatic diseases.

Certain malignant cells possess a genetic aberration in chromosomes 7 (croce et al. *Scientific American*, 238;117–125, 1978) and 13 such that these cells express themselves in an abnormal biosynthesis of two specific enzymes: β-glucuronidase and tyrosinase (Chen et al. *Cancer Research*, 39:3485–3490, 1979). Among these malignant growths are breast cancer, lung cancer, colon cancer, melanoma, and gastric cancer. As disclosed in previously cited Rubin patents, 5,639,737 and 5,475,842, PMPG, or para-methoxy-phenyl-glucuronide, is a "pro-drug" that is substantially non-toxic to healthy cells but becomes cytotoxic to cancerous cells only after two sequential activations by these two specific enzymes, β-glucuronidase and tyrosinase. Since non-cancerous, i.e., healthy, body cells do not exhibit high activity of either of these enzymes, there is no substantial toxicity to healthy body cells.

The molecular structure of PMPG is as follows:

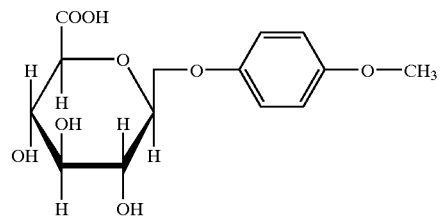

This drug is the glucuronide of para-methoxy-phenol (4-hydroxy anisole). Because it is a glucuronide, PMPG, or Glycosole, possesses a low toxicity to healthy cells. An important mechanism of the liver in detoxification of a variety of toxic phenols is conjugation of these phenols with glucuronic acid, which reaction is catalyzed by glucuronyl transferase.

Once this prodrug, Glycosole, is administered to the patient, Glycosole is hydrolyzed at the cancer site by the first enzyme, β-glucuronidase, to produce para-methoxy-phenol as follows:

Reaction (1)

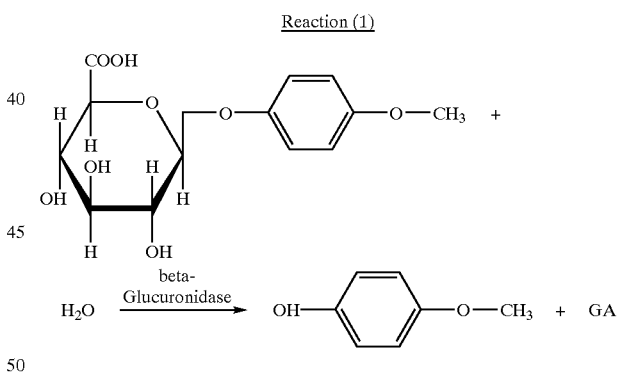

This reaction takes place mainly at the cancer site, because only at the cancer site is the enzyme available to catalyze the reaction (Levvy et al., in *Glucuronic Acid Free and Combined*, G. J. Dutton, ed., Academic Press, NY, 1996, pp. 305–306; and Sweeney et al., Cancer Research, 31:477–478, 1971). It should be emphasized here that in normal cells, β-glucuronidase is a lysosomal-microsomal enzyme. It is only in cancer cells that this enzyme is also membrane linked, and thus can be exposed to the substrate, in this case the Glycosole.

The para-methoxy-phenol that is released from Reaction (1) is now available as a substrate for the second reaction, shown as Reaction (2). Reaction (2) is catalyzed by the enzyme tyrosinase (Morgan et al., *Clinical Oncology*, 7:227–234, 1981; and Kanclerz et al., *Brit. J. of Cancer*, 54:693–698, 1986). Tyrosinase oxidizes the para-methoxyphenol in a series of steps to a toxic molecule, methoxy-ortho-benzoquinone.

Reaction (2)

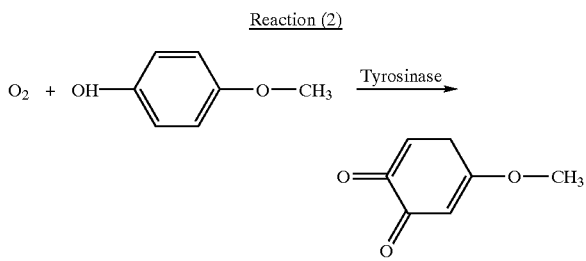

Methoxy-orthobenzoquinone is a strong electrophilic molecule that is able to conjugate sensitive sites on proteins (including enzymes), lipids, and nucleic acids. The "attacked" cancer cell tries to defend itself against the protruder by sacrificing a molecule of glutathione as an electron donor. This reaction, Reaction (3), forms a molecule of mercapturic acid.

Reaction (3)

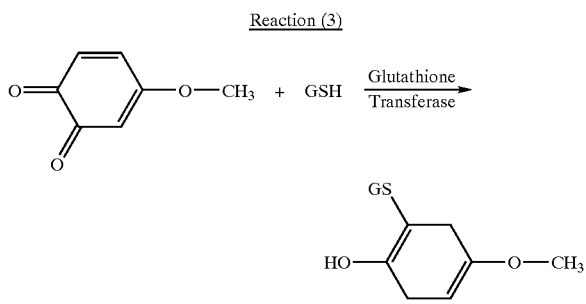

Fortunately, the amount of glutathione available in many cancerous cells is quite limited. Once the glutathione is depleted, the cancerous cell cannot defend itself any more against this oxidizing stress, and the inevitable result is denaturation of the cell. In this reaction, key sulfhydryl groups of different macromolecules are irreversibly conjugated to this highly electrophilic molecule, methoxy-ortho-benzo-quinone, and destroyed.

Some cancer cells, however, are still capable of producing increased levels of glutathione, despite the stress induced by methoxy-ortho-benzo-quinone. This increased production of glutathione tends to protect these cancerous cells from electrophilic molecules such as methoxy-ortho-benzo-quinone. The enzyme glutathione synthetase, the key enzyme in the biosynthesis of glutathione, is an inducible enzyme. That is, in certain stress conditions, such as a vast depletion of glutathione, there is a de novo synthesis of these molecules, (glutathione is a tri-peptide of glutamate-cysteine-glycine), and the cell can still be protected against destruction.

SUMMARY OF THE INVENTION

It is an object of the present invention to overcome the aforesaid deficiencies in the prior art.

It is another object of the present invention to provide a method and composition for treating malignant cells.

It is another object of the present invention to provide a method and composition for treating malignant cells without damaging normal cells.

According to the present invention, malignant cells are treated by administering a combination of (a) a compound that, when acted upon by tyrosinase, is converted to an electrophilic compound or an oxidizing agent, or a saccharide conjugate or a pharmaceutically acceptable ester or salt thereof, and (b) an aldehyde or a compound which is hydrolyzed in the body to an aldehyde. This tyrosinase substrate, which for purposes of the present invention will also be termed a pro-oxidizing agent, may be a compound which, when acted upon by tyrosinase, forms a cytotoxic phenolic compound. Optionally, the combination can include (c) a compound which inhibit the action of glutathione-S-transferase, such as ethacrynic acid.

The pro-oxidizing agent is preferably administered as part of a saccharide conjugate, so that, once in the body, the conjugate at the site Of the tumor is released to form the pro-oxidizing agent by virtue of action of the saccharidase enzymes present in higher concentrations at the tumor site than in the vicinity of healthy cells. Once the pro-oxidizing agent is released from the conjugate, tyrosinase in the vicinity of the cancer cells converts the pro-oxidizing, agent to a cytotoxic oxidizing agent.

The aldehyde can be administered directly, such as by administering glyceraldehyde orally or intravenously. Alternatively, the aldehyde can be administered in the form of a compound which is hydrolyzed in the body to an aldehyde, such as benzylidene. Where the aldehyde or the aldehyde precursor is toxic, the aldehyde or pre-aldehyde is administered as a saccharide as a saccharide conjugate. In the liver, kidney, intestines, and most other organs, the aldehydes are oxidized to the corresponding acids. This oxidation is catalyzed by the enzyme aldehyde dehydrogenase. Aldehyde dehydrogenase acts almost immediately to catalyze the oxidation of the aldehyde, so that the aldehyde is in the body only for an extremely short time, i.e., not long enough to injure healthy cells if the aldehyde itself is toxic. Most cancer cells, however, do not exhibit this aldehyde dehydrogenase activity, and, therefore, the aldehyde molecule is not oxidized at the site of the cancer cells. In return, in many cancerous cells, a non-enzymatic reaction occurs, namely, the formation of an insoluble thiazolidine from the aldehyde and cysteine. Where the aldehyde precursor is benzylidene, this reaction results in the formation of a heterocyclic molecule from benzaldehyde and cysteine, thiazolidine-4-carboxylic acid (Sessa et al., *Cancer Research*, 37:2170–2176, 1977). This reaction is shown as Reaction (4).

Reaction (4)

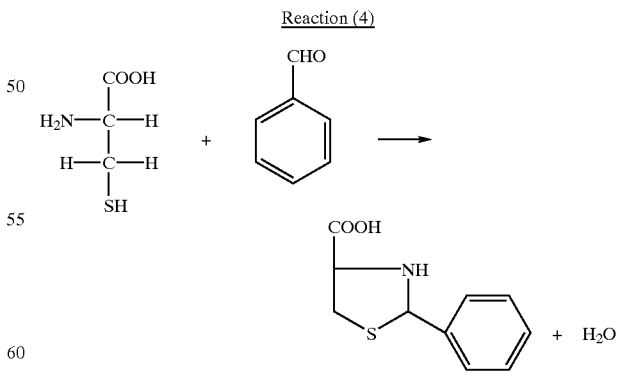

The reaction between the aldehyde and cysteine is irreversible when the reaction product is an insoluble thiazolidine. Therefore, as the reaction progresses, the cysteine in the cancer cell is depleted. Thus, when the cancer cells are treated with an aldehyde precursor, an aldehyde, or a saccharide conjugate thereof, the cancer cells cannot produce any more glutathione, and thus remain defenseless against the devastating effects of the oxidizing agent. Of course, the aldehyde used must be one which produces an insoluble thiazolidine when reacted with cysteine.

It has also been discovered that the depletion of cysteine by itself interferes with the normal metabolism of the cells, and, indeed, benzylidene glucose exhibits some anti-cancer activity on its own against certain types of cancer, as shown in Takeuchi et al., U.S. Pat. No. 4,882,314.

The present invention thus provides a process which is non-toxic to non-cancerous cells that produces compounds which are extremely toxic to cancer cells after two sequential steps of activation and potentiation that can occur only at the cancer site. The aldehyde or precursor is used simultaneously with the oxidizing agent in order to eliminate the capacity of the afflicted cells to neutralize the effect of the oxidizing agent prodrug and thus leave the cancer cells substantially defenseless. Both of the compounds used exhibit minimal or no toxicity to healthy body cells because of different metabolic paths.

DETAILED DESCRIPTION OF THE INVENTION

The present invention provides a method for treating malignant cells by administering a combination of (a) an oxidizing agent, which may be in the form of a saccharide conjugate or a pharmaceutically acceptable ester or salt thereof of an oxidizing agent; and (b) an aldehyde or an aldehyde precursor, each of which may be in the form of a saccharide conjugate or a pharmaceutically acceptable ester or salt thereof. Optionally, ethacrynic acid may also be administered in order further to decrease the capacity of the cell to resist the oxidizing agent. In the preferred embodiment the oxidizing agent is a substrate for tyrosinase.

The oxidizing agents are generally cytotoxic phenolic compounds, many of which are substrates for tyrosinase. Among these oxidizing agents which have been found to be toxic to human tumor cells include tyrosine, 4-propoxy phenol, 4-tert-amyl phenol, 4-hydroxyanisole, butylated hydroxyanisole, L-3,4-dihydroxyphenylalanine, dopamine (3,4-dihydroxyphenethylanine), tert-butylcatechol, hydroquinone, resorcinol, 6-hydroxydopa (3,4,6-trihydroxyphenylalanine), 4-tert-butyl phenol, 4-benzomethoxy phenol, and methyl gallate. These compounds are administered in the form of conjugates of glucuronic acid or saccharides, which conjugates may be made by any convenient means. In some instances, depending upon the type of cancer cells to be treated, the oxidizing agent can be administered alone, or in combination with the conjugated form of the oxidizing agent.

A combination of saccharide conjugates of oxidizing agents can be used in conjunction with the aldehyde or aldehyde precursor, which can be in the form of the free compound or in the form of a saccharide conjugate. As with the oxidizing agents, the saccharides can be chosen to have the maximum effect for the particular tumor treated. For example, melanomas have both α-D-glucosidase activity as well as β-D-glucuronide activity. Therefore, melanomas are preferably treated with an oxidizing agent such as 4-propoxy phenol or 4-tert-amyl phenol which has been conjugated to an α-D-glucoside as well as to β-glucuronide. In order to prevent metastases, one of the saccharides can be lactose. Alternatively, lactose can be administered in conjunction with the saccharide conjugates. Mammary tumors, on the other hand, have a very high β-galactosidase activity, and these tumors are effectively treated by conjugating β-D-galactoside to an oxidizing agent, such as 4-propoxy phenol, 4-hydroxyanisole, or 4-tert-amyl phenol, which can be used in combination with a conjugate of an oxidizing agent which has been conjugated to a β-D-glucuronide. One skilled in the art can readily determine what saccharide enzyme or enzymes activity a particular tumor possesses. The combination of conjugates can then be tailored for optimum destruction of the tumor.

As noted above, the saccharide to be used in the present invention is any saccharide that can be conjugated to an oxidizing agent such as a cytotoxic phenol and which is readily cleaved from the agent by an enzyme particular to a tumor. Thus, the saccharide conjugated to the oxidizing agent can be any saccharide which is readily cleaved from the phenol by an enzyme particular to a tumor. Several, non-limiting, examples of such saccharides include lactose, glucose, galactose, fructose, arabinose, mannose, gulose, ribose, xylose, lyxose, erythrose, maltose, cellobiose, sucrose, and rhamnose.

The conjugates of the oxidizing agents compounds can be used in the acetylated form. That is, when the conjugates are prepared by conjugating an oxidizing agent with methyl (tri-O-acetyl-α-D-glycosyl bromide) uronate, a triacetyl methyl ester is formed. This triacetyl methyl ester can be used in the acetylated form. Since these acetyl groups are not easily removed, the compounds are not particularly cytotoxic to normal cells. However, since primitive cells, such as growing cancer cells, can produce many different types of enzymes, including acetylase, these primitive cells can readily remove the acetyl groups on the acetylated conjugates to provide active forms of the compound directly at the site of a growing tumor. Of particular importance are the tri-acetylated conjugates, since the tri-acetylated conjugates are lipid soluble and are retained by the body at the tumor site for a much longer period of time than the unacetylated conjugates. The tri-acetylated conjugates have also been found capable of crossing the blood-brain barrier.

Of the phenolic conjugates of the present invention, the lucuronide of 4-propoxy phenol, 4-hydroxyanisole and 4-tert-amyl phenol are preferred compound for use with aldehydes or precursors thereof. Because these conjugates are glucuronides, they possess a low toxicity.

The oxidizing agent (either in free or conjugated form, or as a mixture of the two) and the aldehyde or precursor thereof are administered simultaneously in order to eliminate the possibility that the cancer cells will neutralize the effects of the oxidizing agent. Dosages are sufficient to provide from about 1 to 10 grams of the oxidizing agent and from about 1 to about 10 grams of the aldehyde or sufficient precursor to provide from about 1 to about 10 grams of aldehyde. When the oxidizing agent or aldehyde is conjugated to a saccharide, sufficient amount of conjugate must be administered to promote 1–10 grams of oxidizing agent and 1–10 grams of aldehyde.

A number of methods can be used to manufacture the conjugates of the oxidizing agents with saccharides according to the present invention, including those disclosed in Rubin, U.S. Pat. Nos. 4,481,195 and 4,424,348, the entire contents of each of which are hereby incorporated by reference.

More particularly, the oxidizing agent, which is preferably a phenolic compound, is conjugated to the saccharide by conjugation of the phenol group with methyl (tri-O-acetyl-α-D-aglycon bromide) uronate, the active form of the saccharide for conjugation, and may be produced in accordance with the teachings of Bollenback et al., *J. Am. Chem. Soc.,* 7:3310 (1955), the entire contents of which are hereby incorporated by reference.

The phenolic compound is introduced into the methyl (tri-O-acetyl-α-D-aglycon bromide) uronate in a solution of the phenol with a catalytic amount of silver oxide or silver carbonate.

Another method of conjugation is to use sodium or potassium hydroxide as the condensing agent in acetone or methanol solution. A stoichiometric excess of the phenolic compound is maintained at room temperature for 72 hours, or until the reaction to form the triacetyl methyl ester is complete.

The triacetyl methyl enter can be used as such or can be converted to the acid form of the conjugate by reaction with ½ molar amount of 0.5 N of a base such as barium hydroxide, methanolic sodium hydroxide, or sodium methoxide, which base is added slowly to this solution to form a white precipitate. Preferably, an excess of the base is added until there is no more precipitation. The free saccharide is released by adding 0.5 N sulfuric acid, volume to volume, followed by cooling in ice water for 20 minutes. The mixture is then filtered, and the supernatant is dried in vacuum and crystallized from ether.

The triacetylated form of the saccharide conjugate is the preferred form to be used in the present invention. However, the free acid form of the conjugates may also be used when a water-soluble form of the conjugate is desired. Therefore, whenever the term "saccharide conjugate" is used in the present specification and claims, it is understood to include not only the free acid form of the conjugate but also the acetylated conjugates as well as pharmaceutically acceptable salts and esters thereof, as discussed hereinabove.

Ethacrynic acid, [2,3-dichloro-4-(2-methylene-1-oxobutyl)phenoxy]acetic acid, has conventionally been used as a diuretic. However, ethacrynic acid also is highly electrophilic, and reacts with glutathione to form mercapturic acid. When the glutathione reacts with ethacrynic acid, glutathione-S-transferase is inhibited, and the cysteine is tied up so that the cancer cell cannot produce more glutathione.

Thus, according to the present invention, the oxidizing agent is a strong electrophilic molecule that conjugates sensitive sites on proteins. When the cancer cell sacrifices a molecule of glutathione as an electron donor to offset the effect of the oxidizing agent, a molecule of mercapturic acid is formed. Even though the amount of glutathione available in many cancerous cells is limited, some cancer cells are still capable of producing increased levels of glutathione to protect the cells against electrophilic molecules. In certain stress conditions, such as with a vast depletion of glutathione, there is a "rebound" effect, similar to the rebound experienced when excess base is added to the stomach in an attempt to neutralize stomach acid. For cancer cells which can synthesize glutathione after the initial depletion, the glutathione synthesis can be intercepted by depleting the cells' supply of cysteine, one of the building blocks of glutathione, by administering an aldehyde which forms in insoluble thiazolidine with cysteine. The aldehyde reacts with cysteine to form an insoluble thiazolidine, and the optional ethacrynic acid inhibits the action of glutathione-S-transferase, further inhibiting the ability of the cancer cells to produce glutathione.

Once the cancer cells can no longer produce glutathione to take up the electrophilic compounds, i.e., the oxidizing agents, the cancer cells can no longer survive.

For purposes of the present invention, any aldehyde which precipitates with cysteine to form an insoluble compound and thus eliminate and interfere with cancer cells' production of glutathione, can be used. When the aldehydes have low toxicity, they can be used as the aldehydes themselves. However, when the aldehydes are toxic, they can be conjugated to saccharides, where they are deconjugated at the tumor site in the same manner as the oxidizing agents. Examples of aldehydes or aldehyde precursors that can be used in the present invention include glyceraldehyde, benzylidene, pyruvaldehyde, mono-, di-, and tri-hydroxy $C_2$–$C_{20}$ straight- and branched-chain aldehydes, such as beta-hydroxybutyraldehyde, beta-hydroxypentylaldehyde, and the like. These aldehydes are not toxic, and can be used in their free aldehyde form. Other aldehydes that can be used, such as citral and citronal, are too toxic to be used in the free form, but they can be used if they are conjugated to a saccharide.

The selectivity of the saccharide compounds toward tumors can be greatly increased and the possible deconjugation of the cytotoxic phenolic compounds in healthy parts of the body can be further minimized by administering to the patient, prior to or simultaneously with administration of the conjugate, an alkalinizing agent which will maintain the pH of the rest of the body at a pH of about 7.4. Of course, this alkalinizing agent has minimal effect on the pH of the stomach, and it is to be understood that the alkalinizing procedure does not apply to the gastrointestinal tract, where, unlike the rest of the body, the pH may vary substantially from about 7. It is well known that the activity of β-glucuronidase is substantially nil at a pH of 7.4. Thus, administration of alkalinizing agents such as bicarbonates or other basic salts will substantially decrease and eliminate β-glucuronidase activity which occurs naturally in certain healthy tissues such as the kidneys, spleen, and liver. Administration of alkalinizing agents will not increase the pH of the tumor cells themselves, however, because the tumor cells have a pH which is below the pH of the body, the mechanism of prior hyperacidification, and the lack of substantial blood perfusion through the tumor area, as well as other mechanisms. It has been suggested in the literature, in fact, that bicarbonate actually increases the acidity of the cancer cells, cf. Gullino et al. *J.N.C.I.,* 34(6):857–859 (1965).

Since the saccharidase activity of the tumor cells is enhanced by acidification, and the saccharidase activity of the rest of the body, particularly of the kidneys, will be substantially eliminated by alkalinization, the phenolic compound will only be released at the tumor site itself due to deconjugation of the saccharides by the action of the saccharidase. Without the alkalinization step, substantial amounts of toxic materials may be released, for example in the kidneys, and the cytotoxic phenols so released may cause substantial damage to these organs if there is any tyrosinase present at the site. The greater toxicity of the phenols after the action of the tyrosinase, the more important is the alkalinization step.

Other steps for increasing saccharidase activity at the tumor cells can also be undertaken. One method of accomplishing this is to elevate the temperature of the cancer cells at the time of treatment. This may be done by elevating the temperature of the entire body such as by the use of a pyrogenic drug or by elevating the temperatures solely in the area of the tumor cells, for example, by using microwave radiation or electrical current. Raising the temperature increases the saccharidase activity of the cancer cells, thereby increasing the efficiency of the deconjugation of the saccharides. It is known that, in the temperature range of about 35 to 45° C., raising the temperature about 3° C. increases saccharidase activity by up to 50%.

Known pyrogenic drugs that can be administered to raise body temperature include etiocholanolone, progesterone, dinitrophenol, dinitrocresol, and the like. Dinitrophenol and dinitrocresol are preferred for this use because they are cytotoxic. The saccharide conjugates of these compounds are particularly preferred because, when the saccharide is deconjugated at the tumor site, the aglycone will not only act to denature the cytoplasmic protein, but also will raise the temperature directly in the region of the tumor cells, thus greatly increasing the efficiency of further deconjugation.

Local hypothermia in the region of suspected tumor cells is preferred to general hypothermia because general hypothermia will also increase the saccharidase activity in healthy cells. However, because of the alkalinization step, this is not a major problem. If the hypothermia is local, this provides an additional degree of certainty that the glucuronides will only become deconjugated at the tumor site. The application of microwave treatment directed at the suspected tumor site is one way to achieve total hypothermia. Because of the different electrical resistance of tumor cells, another method of achieving some degree of local hypothermia is by administering a low electrical current through the body.

Another way to increase saccharidase activity selectively at tumor cells is by administration of estrogen to female patients or testosterone to male patients, for tumors which are not estrogen- or testosterone-dependent, respectively. It has been reported that these compounds induce saccharidase activity in trophoblastic cells. Since certain tumor cells are known to be trophoblastic, this method is particularly useful for those types of cells. The alkalinization step prevents damage to healthy trophoblastic cells.

Prior to treating patients in accordance with the present invention, it should be ascertained that the particular type of tumor involved has both a high saccharidase activity as well as a high tyrosinase activity. This may be done in a number of ways.

One way is to assay tumor cells obtained in a biopsy for saccharidase activity. If the test is positive, then the oxidizing agents and the aldehydes or precursors thereof can be administered in the form of the appropriate saccharide conjugates. More particularly, by ascertaining the particular saccharidase activity of the tumor cells, one can select the particular saccharide conjugate or mixture of saccharide conjugates which will most effectively treat the tumor cells. By using a conjugate or conjugates which are cleaved by the saccharidase(s) most abundant in the tumor cells, one can maximize the amount of oxidizing agent and/or aldehyde delivered directly to the tumor site.

Alternatively, where the tumor cells do not have a high saccharidase activity, the oxidizing agent and/or aldehyde can be administered as the free compounds.

A second method is the administration of a saccharide whose aglycone has been labelled with a radioactive isotope. If, upon a full body scan, it is found that the radioisotope has accumulated at any specific areas of the body, then this indicates not only the location of the tumor but the fact that the tumor has sufficient saccharidase activity to deconjugate the saccharide. After this has been determined, the appropriate amount of the appropriate saccharide conjugate(s) of choice may be administered. If there are no tumors present, or the tumors are of the type which do not have saccharidase activity, then there will be no accumulation of radioisotope in the body, as the alkalinization step of the present invention eliminates all saccharidase activity, and the isotope will be passed through the body. For these types of tumors, the oxidizing agent and the aldehyde are administered in the form of the unconjugated compounds.

Another method for determining which saccharide(s) should be used to form the conjugates is to test for the presence of free glucuronic acid in the urine. While the presence of glucuronides in the urine is common, the presence of free glucuronic acid in the urine, and particularly the presence of increasing amounts of glucuronic acid when tested over a period of several days, is a potent indication of the presence of tumors with β-glucuronidase activity. It has been hypothesized that the presence of free glucuronic acid in the urine in cancer patients is caused by the action of β-glucuronidase in the cancer cells on the intercellular filaments and connective tissue. Glucuronic acid is a reaction product of such activity because the intercellular filaments and connective tissues are composed of polymers of which glucuronic acid is an element, and which are a known substrate for the enzyme β-glucuronidase.

A method for distinguishing free glucuronic acid from conjugated glucuronides in the urine was disclosed in Rubin, U.S. Pat. No. 4,337,760, the entire contents of which are hereby incorporated by reference. In the urine test for glucuronidase activity, normal patients exhibit between 200 and 50 mg per 24 hours of free glucuronic acid in the urine. Cancer patients with well-developed tumors which have β-glucuronidase activity show greater than 2000 to 7000 mg per 24 hours of free glucuronic acid. Accordingly, if a patient exhibits more than about 600 mg per 24 hours of free glucuronide, this is an excellent. indication of the presence of tumors having a high β-glucuronidase activity.

A negative indication on this urine test does not conclusively rule out the presence of tumors having β-glucuronidase activity, because tumors in their initial stages, although they might have β-glucuronidase activity, might not release sufficient free glucuronic acid to cause a positive reading in the urine. Therefore, the urine test should be repeated, and if an increasing amount of free glucuronic acid is found, this is another indication of the presence of a tumor having β-glucuronidase activity.

Although 4-hydroxyanisole and other oxidizing agents may not generally be toxic to healthy cells, when these substances are acted upon by tyrosinase they are converted to toxic metabolites which have their dominant effect inside the cells, where they are produced (i.e., melanoma cells and melanocytes), as tyrosinase converts a number of phenols (e.g., its natural substrate, tyrosine) to catechols and quinones which react strongly with SH groups.

Tyrosinase activity of tumor cells can be determined by assaying a sample obtained from a biopsy by the method of Pomerantz, *J. Biol. Chem.,* 241:161 (1966), using L-[3,5-$3^H$]-tyrosine (Amersham TRK 200). Using this method, Wallevki et al., op. cit, determined that melanotic melanoma had the greatest tyrosinase activity, while bladder carcinoma and amelanotic melanoma had less but measurable tyrosinase activity. Skin fibroblasts were found to have no tyrosinase activity.

The amount of active ingredients administered to a patient in the form of saccharide conjugates depends upon the amount of saccharidase activity of the tumor. The greater the amount of saccharidase activity of the tumor, the greater the proportion of the active ingredients that can be delivered as saccharide conjugates, up to 100% of saccharide conjugates.

In order to alkalinize the patient prior to treatment, a dose of glucose, such as 100 grams of honey, glucose, or other simple sugar is administered, generally via intravenous drip of about a 10% aqueous solution of glucose and 60 milliequivalents sodium bicarbonate. Approximately one liter of this solution is administered, assuming no contraindications, and the pH of the urine is checked to determine that it has reached a pH of approximately 7.4. This establishes that the system has become alkalinized, and it is now safe to administer the glucuronide. Another liter of the same glucose-bicarbonate solution containing the desired amount of oxidizing agent and aldehyde or aldehyde precursor, either in the free form or in the conjugate form, is then administered. This administration is repeated daily as needed. It is desirable to maintain high levels of glucose in the blood during treatment according to the present invention, unless the saccharide of the conjugates used is glucose, of course. When glucose levels in the blood are increased, they are generally increased to at least 180%, and preferably about 250%, of normal.

When galactose is the saccharide of choice, exogenous galactose should not be administered to the patient, such as from dairy products. In the same manner, when the conjugate of another saccharide is administered, the patient should not receive exogenous saccharide so that the saccharidase activity can be centered on the conjugate, and not on exogenous saccharide.

If there are contraindications for the administration of bicarbonate parenterally, an antacid may be administered orally. This antacid may be any conventional antacid, such as sodium bicarbonate, magnesium bicarbonate, aluminum hydroxide, aluminum magnesium silicate, magnesium carbonate, magnesium hydroxide, magnesium oxide, or the like. The important criterion is that the pH of the urine become approximately 7.4 and remain so during treatment.

The hyperacidification of the tumor cells is caused by a hyperglycemic condition in the patient. Therefore, any hyperglycemic agent may be used as the hyperacidification agent, such as, for example, fructose, galactose, lactose, or glucagon. Furthermore, it should be understood that this hyperglycemic condition may be effected in any known manner. For example, if the patient is diabetic, then the condition can be brought about by decreasing the insulin administration. Of course, the hyperacidification agent should not be the same saccharide as in the conjugate to be administered.

Any agent which will raise the pH of the urine to approximately 7.4 can be used as the alkalinizing agent, including sodium or potassium bicarbonate or citrate, or other basic salts or antacids. While it is preferred that these agents be administered intravenously, they may be administered orally.

When the term "approximately 7.4" is used in the present specification and claims with respect to the pH level to be maintained in the rest of the body, it should be understood that a pH level slightly above or below 7.4 may be used, although 7.4. is the preferred pH. Of course, this pH does not apply to the gastrointestinal tract, where the pH may vary substantially from about 7. As the pH decreases from 7.4, the β-glucuronidase activity increases until the optimal pH is reached. Furthermore, below pH 7.0 the remainder of the body will not be alkaline but will be acid. Above 7.4 the danger of alkalosis increases without any substantial further decrease in β-glucuronidase activity. A pH level of 7.4 is preferred, as this is physiological pH and cannot be harmful to the body; it is known that the β-glucuronidase activity in healthy organs is substantially nil at this pH level.

The dosage of the compounds administered should be monitored to avoid any side effects due to the massive release of toxins caused by the dying cancer cells. It may be preferable to treat the patient with the compounds of the present invention in short courses of several days, leaving several days in between to allow any toxins released by the dying cancer cells to leave the body before continuing with treatment.

When a conjugate of lactose with an oxidizing agent is administered, it must not be administered orally. Intramuscularly is a preferred method of administration, with the lactose dissolved in a suitable carrier such water. When the lactose is administered as part of a conjugate, the amount to be administered depends on the particular oxidizing agent used. However, one skilled in the art can readily determine the optimum amount of the conjugate to be administered, taking into account the patient's condition, the size of the tumor, etc. For example, using New Drug Exemption Guidelines published by governmental authorities, one skilled in the art can readily establish preclinical and clinical trials for determining the preferred dosages to be used. One skilled in the art would, using methods described in standard textbooks, guidelines, and regulations as described above, as well as common general knowledge within the field, be able to select the exact dosage regimen to be implemented for any sleeted conjugate using merely routine experimentation procedures.

In determining dosages of the conjugates to be administered, the dosage and frequency of administration is selected in relation to the pharmacological properties of the specific active ingredients or conjugates. Normally, at least three dosage levels should be used. In toxicity studies in general the highest dose should reach a toxic level but be sublethal for most animals in the group. If possible, the lowest dose should induce a biologically demonstrable effect. These studies should be performed in parallel for each conjugate selected.

Additionally, the $ID_{50}$ level of the active ingredient or conjugate thereof in question can be one of the dosage levels selected and the other two selected to reach a toxic level, and the lowest dose one that does not exhibit a biologically demonstrable effect, e.g., destruction of the tumor. The toxicology tests should be repeated using appropriate new doses calculated on the basis of the results obtained. Young, healthy mice or rats belonging to a well-defined strain are the first choice of species, and the first studies use the intramuscular, the preferred, route of administration. Control groups given a placebo or which are untreated are included in the tests. Tests for general toxicity, as outlined above, should normally be repeated in another non-rodent species, e.g., a rabbit or a dog. Studies may also be repeated using other routes of administration.

Further, single dose toxicity tests should be conducted in such a way that signs of acute toxicity are revealed and the mode of death determined. The dosage to be administered is calculated on the basis of the results obtained in the above-mentioned toxicity tests. It may be desired not to continue studying all of the initially selected conjugates or active ingredient. Data on single dose toxicity, e.g., $ID_{50}$, the dosage at which half of the experimental animals die, is to be expressed in units of weight or volume per kg of body weight and should generally be furnished for at least two species with different modes of administration. In addition to the $LD_{50}$ value in rodents, it is desirable to determine the highest tolerated dose and/or lowest lethal dose for other species, e.g., dog and rabbit.

When a suitable and presumably safe dosage level has been established as outlined above, studies on the drug's chronic toxicity, its effect on reproduction, and potential mutagenicity may also be required in order to ensure that the calculated appropriate dosage range will be safe, also with regard to these hazards.

Pharmacological animal studies on pharmacokinetics revealing, e.g., absorption, distribution, biotransformation, and excretion of the conjugate or active ingredient and metabolites are then performed. Using the results obtained, studies on human pharmacology are then designed. Studies of the pharmacodynamics and pharmacokinetics of the conjugates in humans should be performed in healthy subjects using the routes of administration intended for clinical use, and can be repeated in patients. The dose-response relationship when different doses are given, or when several types of conjugates or combinations of conjugates and free compounds are given, should be studied in order to elucidate the dose-response relationship (dose vs. plasma concentration vs. effect), the therapeutic range, and the optimum dose interval. Also, studies on time-effect relationship, e.g., studies into the time-course of the effect and studies on different organs in order to elucidate the desired and undesired pharmacological effects of the drug in particular on other vital organic systems should be performed.

The compositions of the present invention are then ready for clinical trials to compare the efficacy of the conjugate to existing therapy. A dose-response relationship for therapeutic effect and for side effects can be more finely established at this point.

Besides intravenous administration, the acid form of the conjugates may be administered by any means of parenteral administration. However, the free acid form of the glucuronides should not be administered orally, as it is known that β-glucuronidase is present in the digestive tract. The tri-acetylated conjugates, however, can be administered orally, as the β-glucuronidase in the digestive tract does not affect the acetylated conjugates.

The amount of compositions of the present invention to be administered to any given patient must be determined empirically and will differ depending upon the condition of the patient. Relatively small amounts of the conjugates can be administered at first, with steadily increasing dosages if no adverse effects are noted. Of course, the maximum safe toxicity dosage as determined in routine animal toxicity tests should never be exceeded.

Optimally, the concentration of active ingredients to be administered, whether as conjugates or as free compounds, should be sufficient to provide a concentration of approximately $5 \times 10^{-4}$ M to about $5 \times 10^{-3}$ M of oxidizing agent and approximately 0.05 to 10 mM of aldehyde. The optional ethacrynic acid is administered in an amount of from about 25 mg/kg to about 150 mg/kg.

It is clear that almost any type of tumor cells can be treatable in accordance with the present invention, with the remaining organs of the body protected by the alkalinization step when saccharide conjugates are used. Tumors which are known to have saccharidase activity, and for which the saccharide conjugates are particularly effective, include solid breast tumors and their metastases, bronchogenic carcinoma and its metastases, and lymphomas, as well as lung carcinoma including non-small cell carcinoma and squamous cell carcinoma, colon carcinoma, testicular carcinoma, hepatic carcinoma, pancreatic carcinoma, ovarian carcinoma, leukemia, prostate carcinoma and rectal carcinoma. Hodgkin's disease can also be treated by the method and composition of the present invention. Tumors which have high tyrosinase activity, as noted above, include melanoma, amelanotic melanoma, breast carcinoma, and bladder carcinoma, as well as a number of the other tumors noted above.

When it is desired to induce hypothermia to increase saccharidase activity, a method should be selected by which the temperature is raised as much as possible without risking damage to healthy portions of the body, such as the eyes. An increase of about 2° C. of whole body hypothermia, and as much as 4.5° C. for local hypothermia, is preferred. The hypothermia should be timed to last about one hour at the time of greatest saccharide concentration at the tumor site. For example, when local microwave treatment is selected, it should begin about one half hour after commencement of the intravenous conjugate drip and be continued for about one hour. The proper dosage of known pyrogens to achieve the desired degree of hypothermia is known to those skilled in the art, and can be easily empirically determined without undue experimentation. A dosage of about 30 ng/day of dinitrophenol, for example, would be appropriate.

Because the triacetylated form of the conjugate is not affected by saccharidase in the digestive tract, this form of the the conjugates can be administered orally without loss of activity. Moreover, it has been found that, because the triacetylated form of the conjugates is lipid soluble, the triacetylated form of the conjugate is retained in the body for a much longer time than the free acid form of the conjugate. The tri-acetylated form of the conjugate provides an additional level of protection for normal cells, since the active compounds are not released in the body until the acetyl groups are removed and the saccharide is removed from the conjugate. Since primitive cells such as cancer cells produce acetylase, this acetylase removes the acetyl groups from the conjugate. The more anaplastic (i.e., more immature) the tumor cells, the more enzymes they produce, so that the triacetylated form of the drug is more selectively toxic to tumor cells than even the conjugated form. Thus, since two steps are required to liberate the phenolic compound, the conjugates are even more preferentially delivered to the site of an active tumor than the acid form of the conjugates.

When estrogen or testosterone are administered, a dose of from about 3–15 mg/kg body weight/day provides the desired inducement to saccharidase activity.

To treat a patient suffering from cancer, the oxidizing agent and the aldehyde or aldehyde precursor are administered in the form of free compounds, saccharide conjugates, triacetylated saccharide conjugates, or any appropriate mixture thereof. When administered solely as the free compounds or as saccharide conjugates per se, the conjugates must be administered parenterally. However, when the active ingredients are administered in the form of acetylated conjugates, the conjugates can be administered orally, most conveniently in the form of capsules.

Capsules are formulated generally containing approximately 0.1–1 gram of acetylated oxidizing agent saccharide or 0.1–1 gram of aldehyde or precursor thereof saccharide per capsule. The dosage is generally about five to ten capsules of each active ingredient, three times daily, providing about 5 to 30 grams of each active ingredient daily. The patient's serum is measured after a loading dosage of the conjugate is administered to maintain a level of approximately 0.1–1 mM of combined active ingredients in the patient's serum.

Para-methoxyphenyl glucuronide is one preferred oxidizing agent to be used with an aldehyde according to the present invention. This compound is preferred because it is particularly non-toxic to the healthy cells. However, it has been found that 4-propoxy phenyl glucuronide is six times more toxic to cancer cells in vitro than para-methoxy phenol, and 4-tert-amyl phenyl glucuronide is 5.5 times more toxic to cancer cells in vitro than para-methoxy phenol. As with other saccharide compounds of the present invention, the glucuronides can be used in either the triacetylated form or in the free acid form.

When a saccharide conjugate of an active ingredient is used, the prodrug is hydrolyzed at the cancer site by the appropriate saccharidase to yield the active ingredient. This reaction takes place only at the cancer site because only at the cancer site is the saccharidase enzyme available to catalyze the reaction. The second reaction is catalyzed by the enzyme tyrosinase to oxide, e.g., paramethoxy phenol, to a toxic molecule, methoxy orthobenzoquinone. Likewise, 4-propoxy phenol is oxidized to the even more toxic molecule, propoxy orthobenzoquinone, and 4-tert-amyl phenol is oxidized to the extremely toxic molecule 4-tert-amyl orthobenzoquinone. These substituted orthobenzoquinones are strongly electrophilic molecules that conjugate sensitive sites on proteins. When the cancer cell produces glutathione to donate electrons to the substituted orthobenzoquinone, mercapturic acid is formed, and the cancer cell cannot defend itself any further against the oxidizing stress. However, as noted previously, in some cancer cells, there is a "rebound" effect, in which the cell once again can produce glutathione. When an aldehyde or precursor thereof is administered, e.g., glyceraldehyde or benzylidene glucose, if a precursor is used, the body hydrolyzes the precursor to the aldehyde which is then oxidized to the corresponding acid, which oxidation is catalyzed by the enzyme aldehyde dehydrogenase. Since most cancer cells do not exhibit aldehyde dehydrogenase activity, the aldehyde molecule is not oxidized at the cancer site. Then, in many cancerous cells, cysteine reacts with the aldehyde to form an insoluble thiazolidine-4-carboxylic acid. Since this thiazolidine-forming reaction is irreversible, the storage of cysteine in the cancer cell is depleted, and thus, the cells cannot produce additional glutathione to overcome the electron—withdrawing properties of the oxidizing agent.

When conjugates of the active ingredients are used, the conjugates are hydrolyzed by the saccharidase produced by tumor cells to release the active form of the compound at the site of the tumor. The pH for optimal enzymatic activity for most saccharides is about 5.5, so that acidification of the tumor is desirable. This acidification of the tumor, as described elsewhere in this specification, can be achieved by administering glucose to the patient thirty minutes prior to the treatment, as orally administered glucose expresses itself in acidification of the tumor due to accumulation of lactic acid. Of course, if the prodrug conjugate used is a glucose conjugate, an acidification compound other than glucose is administered.

In a preferred treatment protocol, the patient is preferably on a maintenance dosage of a corticosteroid, such as 4 mg of dexamethasone, throughout the duration of the treatment. This dosage ensures delay in premature fibrotic changes and interference with the blood and drug supply to the tumor. Of course, any of the conventional corticosteroids can be used for this purpose.

It should be noted that corticosteroids inhibit the production of tumor necrosis factor, and thus, reduce the malaise, loss of appetite, and cachexia that accompany malignant diseaes. In addition, corticosteroids help in maintaining high levels of blood glucose, and for brain tumors, a higher dosage is useful. Omeprazole, Zantac, Cimetidine, or other anti-ulcer drugs should also be administered concomitantly to prevent ulcers, since corticosteroids are known to induce ulcers. During therapy according to the present invention, no vitamin C supplementation or any ascorbate should be administered to the patient. Ascorbates, being antioxidants, protect the malignant cells from the oxidative damage caused by the oxidizing agents. Any vitamin E administered also acts as an antioxidant, and thus, vitamin E supplementation should be avoided during treatment.

Additionally, during therapy no compounds for acting on the conjugate administered should be administered which are substrates for the enzyme of the tumor to be treated. For example, if the conjugate used is a conjugate with galactose, the patient should avoid ingesting galactose-containing foods. Likewise, where glucose is the conjugate, glucose-containing foods should be avoided.

Although it has been found that by maintaining a serum level of combined oxidizing agent and aldehyde of about 0.1 to 1 mM, serum levels ranging from about 0.05 to about 10 mM can be used, depending upon the patient's response to the treatment. As noted above, one skilled in the art can readily ascertain what saccharide or saccharides should be used to prepare conjugates to treat a particular tumor, and can tailor the prodrugs accordingly. As noted above, synergistic effects can be obtained by combining conjugates. Some of these synergistic combinations include conjugates of β-glucuronides with galactosides for treating mammary tumors, and α-glycosides with β-glucuronides for treating melanomas. Determination of preferred combinations for each tumor type is well within the skill of the art.

More specifically, capsules can be prepared containing about 0.5 gram of a triacetylated saccharide of at least one oxidizing agent and about 0.5 gram of at least one aldehyde or precursor thereof. Examples of these active ingredients are the triacetylated form of propoxy phenyl glucuronide and/or tert-amyl phenyl glucuronide along with benzylidene. In order to prevent formation of glutathione, capsules containing about 0.5 gram of ethacrynic acid can also be administered with capsules of the other active ingredients. The ethacrynic acid reacts with glutathione to form mercapturic acid and inhibit glutathione-S-transferase, tying up cysteine so that the cancer cells cannot produce more glutathione.

The conjugates can be incorporated in any conventional solid or liquid pharmaceutical formulation in any concentration desired. For example, injectable compositions, compositions which may be adsorbed through the mucosa, or transdermally administrable solutions may be used. The pharmaceutical formulations of the invention comprise an effective amount of the conjugates or their analytes.

In addition to the pharmacologically active ingredients or conjugates thereof, the new pharmaceutical preparations may contain suitable pharmaceutically acceptable carriers comprising excipients and auxiliaries which facilitate processing of the conjugates into preparations which can be used pharmaceutically. These compositions, such as suppositories for rectal administration, as well as suitable solutions for administration by injection or by parenteral administration, contain from about 0.01–99%, preferably from about 20 to 75%, of active compound, together with the excipient.

Pharmaceutical preparations which can be used rectally include, for example, suppositories which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parental administration include aqueous solutions of lactose or of a combination of lactose and a water-soluble form of the conjugate. In addition, suspensions of the active compounds as appropriate oily injection suspensions may also be administered. Suitable lipophilic solvents or vehicles include fatty oils, such as sesame oil, or synthetic fatty acid esters, such as ethyl oleate or triglycerides. Aqueous injection suspensions that may contain substances which increase the viscosity of the suspension include sodium carboxymethyl cellulose, sorbitol, and/or dextran.

Administration may be by parenteral, subcutaneous, intravenous, intramuscular, intraperitoneal, or transdermal routes. As noted above, the dosage administered will depend upon the age, health, and weight of the recipient, types of concurrent treatment, if any, frequency of treatment, and the nature of the effect desired.

Each formulation according to the present invention may additionally comprise inert constituents, including pharmaceutically acceptable carriers, diluents, fillers, salts, and other materials well known to the art, the selection of which depends on the dosage form used, the particular purpose to be achieved according to the determination of the ordinary skilled artisan in the field, and the properties of such additives. Examples of carriers and diluents include carbohydrates, lipids, and water.

The active ingredients, either as free compounds or as conjugates, acetylated or not, can be combined with a pharmaceutically acceptable carrier therefore, and optionally other therapeutic and/or prophylactic ingredients. The carriers must be "acceptable" in the sense of being compatible with the other ingredients of the formulation, as well as not being deleterious to the recipient thereof.

Pharmaceutical formulations suitable for oral administration of the conjugates wherein the carrier is a solid are most preferably presented as unit dose formulations such as boluses, capsules, and the like, as well as sachets or tablets, each containing a predetermined amount of active ingredients. A tablet may be made by compression or molding, optionally with one or more accessory ingredients. Compressed tablets may be prepared by compressing in a suitable machine the mixture of active ingredients or conjugates thereof in a free-flowing form, such as powder or granules, optionally mixed with a binder, lubricant, interdiluent, lubricants, surface active, or dispersing agent. Molded tablets may be made by molding the active conjugate with an inert liquid diluent. Tablets may be optionally coated and, if uncoated, may optionally be scored. Capsules may be prepared by filling the active conjugate, either alone or in admixture with another conjugate and/or with one or more accessory ingredients, into the capsule cases and then sealing them in the usual manner. Sachets are analogous to capsules, wherein the active ingredients, together with any optional accessory ingredients, are sealed in a rice paper envelope.

Pharmaceutical formulations suitable for oral administration of the conjugates in which the carrier is a liquid may conveniently be presented as a solution in a pharmaceutically acceptable solvent which is inert to the conjugates included therein.

Pharmaceutical formulations suitable for parenteral administration are conveniently presented in unit dose or multidose containers which are sealed after introduction of the formulation unit required for use.

It should be understood that in addition to the aforementioned carrier ingredients, the pharmaceutical formulations described above may include, as appropriate, one or more additional carrier ingredients such as diluents, buffers, lubricants, preservatives, and the like and substances included for the purpose of rendering the formulation isotonic with the blood of the intended recipient.

The pharmaceutical formulations may be formulations in which the active ingredients may be administered, and include those suitable for oral or parenteral (including intramuscular and intravenous) administration. The formulations may, where appropriate, be conveniently presented in discrete dosage units and may be prepared by any of the methods known in the art of pharmacy. All of the methods include the step of bringing into association the active compounds with liquid carriers or finely divided solid carriers, or both, and then, if necessary, shaping the product into the desired formulation.

Experimental

EXAMPLE 1

A twelve month study was conducted comparing the anti-cancer effect of Glycosole (Glyc., the glucuronide of para-methoxy-phenol), benzylidene-glucose (BG), and a combination of the two compounds (BG+Glyc.). These compounds were administered to patients suffering from prostate cancer separately and together.

All of the patients suffered from bone metastases and no longer responded to conventional hormone therapy.

Patients were administered either 2.4 grams benzylidene glucose per day, 6 grams per day of Glycosole, or a combination of both agents. None of the patients administered benzylidene glucose responded to the treatment. Many of the patients administered Glycosole responded, but all of the patients responded well to administration of the combination of benzylidene glucose and Glycosole.

The results are summarized in Table 1:

| Treatment | Patient No. | P.S.A. Levels during 12 month from initiation of treatment | | | | | | | | | | | |
|---|---|---|---|---|---|---|---|---|---|---|---|---|---|
| | | 1 mo. | 2 mo. | 3 mo. | 4 mo. | 5 mo. | 6 mo. | 7 mo. | 8 mo. | 9 mo. | 10 mo. | 11 mo. | 12 mo. |
| BG. | 1 | 350 | 350 | 370 | 500 | 860 | # | | | | | | |
| | 2 | 120 | 110 | 60 | 200 | 200 | 250 | 250 | 300 | 375 | 380 | 920 | # |
| | 3 | 700 | 550 | 750 | 1100 | # | | | | | | | |
| | 4 | 90 | 80 | 95 | 190 | 210 | 255 | 340 | 380 | 380 | 480 | 700 | 846 |
| | 5 | 890 | 1180 | 1050 | # | | | | | | | | |
| | 6 | 70 | 78 | 80 | 112 | 120 | 170 | 170 | 200 | 220 | 600 | # | |

-continued

| Treatment | Patient No. | P.S.A. Levels during 12 month from initiation of treatment | | | | | | | | | | |
|---|---|---|---|---|---|---|---|---|---|---|---|---|
| | | 1 mo. | 2 mo. | 3 mo. | 4 mo. | 5 mo. | 6 mo. | 7 mo. | 8 mo. | 9 mo. | 10 mo. | 11 mo. | 12 mo. |
| Glyc. | 7 | 480 | 400 | 290 | 280 | 200 | 160 | 180 | 170 | 180 | 200 | 210 | 215 |
| | 8 | 150 | 70 | 65 | 42 | 30 | 30 | 22 | 18 | 13 | 9 | 12 | 24 |
| | 9 | 3800 | 1080 | 540 | 500 | 430 | 320 | 300 | 360 | 365 | 380 | 350 | 420 |
| | 10 | 60 | 50 | 24 | 9 | 8 | 8 | 12 | 20 | 18 | 22 | 22 | 34 |
| | 11 | 240 | 240 | 280 | 300 | 350 | 380 | 410 | 570 | # | | | |
| | 12 | 780 | 700 | 430 | 400 | 360 | 360 | 320 | 260 | 265 | 240 | 180 | 120 |
| BG + | 13 | 1050 | 230 | 140 | 90 | 12 | 12 | 6 | 4 | 4.2 | 3.1 | 7 | 2.2 |
| Glyc. | 14 | 120 | 40 | 1.2 | 1.1 | 0.9 | 1 | 1.1 | 1.3 | 1 | 1.2 | 0.8 | 1.1 |
| | 15 | 322 | 300 | 120 | 96 | 18 | 16 | 14 | 16 | 9 | 12 | 9 | 6 |
| | 16 | 220 | 106 | 85 | 70 | 62 | 40 | 40 | 40 | 46 | 60 | 68 | 64 |
| | 17 | 860 | 620 | 400 | 380 | 120 | 68 | 60 | 44 | 44 | 38 | 36 | 40 |
| | 18 | 105 | 1.2 | 1.1 | 1 | 1.1 | 1 | 2.4 | 2.1 | 2 | 2.1 | 1.3 | 1.3 |

(# Death)

EXAMPLE 2

A six month study was conducted comparing the anti-cancer effect of Glycosole (Glyc., the glucuronide of para-methoxy-phenol), glyceraldehyde, and a combination of the two compounds. These compounds were administered to patients suffering from prostate cancer separately and together.

All of the patients suffered from bone metastases and no longer responded to conventional hormone therapy.

Patients were administered either 3 grams glyceraldehyde per day, 6 grams per day of Glycosole, or a combination of both agents. None of the patients administered glyceraldehyde alone responded to the treatment. Many of the patients administered Glycosole responded, but all of the patients responded well to administration of the combination of glyceraldehyde and Glycosole.

The results are summarized in Table 2:

| Treatment | Patient No. | P.S.A. Levels during 6 month from initiation of treatment | | | | | | | | | | |
|---|---|---|---|---|---|---|---|---|---|---|---|---|
| | | 1 mo. | 2 mo. | 3 mo. | 4 mo. | 5 mo. | 6 mo. | 7 mo. | 8 mo. | 9 mo. | 10 mo. | 11 mo. | 12 mo. |
| Glycer | 1 | 760 | 680 | 600 | 580 | 540 | 420 | | | | | | |
| Aldehyde | 2 | 190 | 180 | 150 | 145 | 140 | 100 | | | | 380 | 920 | # |
| | 3 | 2250 | 1100 | 1000 | 980 | # | | | | | | | |
| | 4 | 340 | 380 | 310 | 280 | 220 | 180 | | | | 480 | 700 | 846 |
| | 5 | 910 | 850 | 740 | 760 | 680 | 360 | | | | | | |
| | 6 | 150 | 90 | 80 | 80 | 64 | 60 | | | | 600 | # | |
| Glyc. | 7 | 480 | 400 | 290 | 280 | 200 | 160 | 180 | 170 | 180 | 200 | 210 | 215 |
| | 8 | 150 | 70 | 65 | 42 | 30 | 30 | 22 | 18 | 13 | 9 | 12 | 24 |
| | 9 | 3800 | 1080 | 540 | 500 | 430 | 320 | 300 | 360 | 365 | 380 | 350 | 420 |
| | 10 | 60 | 50 | 24 | 9 | 8 | 8 | 12 | 20 | 18 | 22 | 22 | 34 |
| | 11 | 240 | 240 | 280 | 300 | 350 | 380 | 410 | 570 | # | | | |
| | 12 | 780 | 600 | 430 | 400 | 360 | 360 | 320 | 260 | 265 | 240 | 180 | 120 |
| Glycosol + | 13 | 1400 | 220 | 68 | 10 | 2 | 1.8 | | | | | | |
| Glycer | 14 | 70 | 6 | 1 | 1.2 | 0.9 | 1 | | | | | | |
| Aldehyde. | 15 | 320 | 110 | 56 | 24 | 9 | 5 | | | | | | |
| | 16 | 460 | 230 | 60 | 34 | 12 | 7.2 | | | | | | |
| | 17 | 23 | 25 | 14 | 6 | 2 | 1.4 | | | | | | |
| | 18 | 1320 | 1100 | # | | | | | | | | | |

(# Dead)

EXAMPLE 3

Ten patients suffering from prostate cancer, ranging in age from 52 to 84, had levels of prostate specific antigen (PSA) ranging from 16 to 1280. These patients were treated with a combination of the glucuronide of 4-hydroxy anisole (PMPG), and benzylidene glucose. The patients were administered capsules containing 0.5 gram of PMPG and 0.5 gram of benzylidene per capsule. Five to ten capsules of each active ingredient, based on the patients' body weight, were administered three times daily for two months. The patients' sera were measured after a loading dosage of the conjugate was administered to maintain a level of approximately 0.1–1 mM of combined active ingredients in each patient's serum.

After two months of treatment, the PSA levels of all ten patients dropped to less than four, which is well within the normal range. After two more months, most patients returned to normal activities.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus the expressions "means to . . ." and "means for . . .", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation.

What is claimed is:

1. A method for selectively treating tumor cells including depleting cysteine in the tumor cells comprising administering to a patient afflicted with a malignant tumor an effective amount of a combination of at least one oxidizing agent which is a substrate for tyrosinase and at least one aldehyde or precursor thereof, which aldehyde forms an insoluble thiazolidine with cysteine and thereby depletes the cysteine in the cancer cells.

2. The method according to claim 1 wherein the combination further includes a compound which inhibits glutathione-S-transferase.

3. The method according to claim 1 wherein the compound which inhibits glutathione-S-transferase is ethacrynic acid.

4. The method according to claim 1 wherein at least one of said oxidizing agent and said aldehyde or precursor thereof is in the form of a saccharide conjugate or an acetylated derivative thereof.

5. The method according to claim 4 wherein the acetylated derivative is a tri-acetylated derivative.

6. The method according to claim 1 wherein the oxidizing agent is selected from the group consisting of 4-propoxy phenol, tyrosine, 4-hydroxyanisole, butylated hydroxyanisole, L-3,4-dihydroxyphenylalanine, dopamine, tert-butylcatechol, hydroquinone, resorcinol, 6-hydroxydopa, 4-tert-butyl phenol, 4tert-amyl phenol, 4-benzomethoxyphenol, and methyl gallate.

7. The method according to claim 1 wherein the aldehyde or precursor thereof is selected from the group consisting of glyceraldehyde, benzylidene, pyruvaldehyde, mono-, di-, and tri-hydroxy $C_2$–$C_{20}$ straight- and branched-chain aldehydes, citral, and citronal.

8. The method according to claim 7 wherein the aldehyde or precursor thereof is glyceraldehyde.

9. The method according to claim 1 wherein the aldehyde or precursor thereof is benzylidene.

10. The method according to claim 1 wherein the aldehyde or precursor thereof is 4,6,0-benzylidene-D-glucopyranose.

11. The method according to claim 4 wherein the saccharide is selected from the group consisting of glucuronides, glucose, galactose, fructose, arabinose, mannose, gulose, ribose, xylose, lyxose, erythrose, maltose, cellobiose, lactose, sucrose, N-acetylglucosamine, acetylgalactosamine, rhamnose, and mixtures thereof.

12. A composition for selectively treating tumor cells comprising an effective amount of a combination of at least one oxidizing agent which is a substrate for tyrosinase and at least one aldehyde or precursor thereof, which aldehyde forms an insoluble thiazolidine with cysteine in a pharmaceutically acceptable carrier.

13. The composition according to claim 12 further including a compound which inhibits glutathione-S-transferase.

14. The composition according to claim 12 wherein the compound which inhibits glutathione-S-transferase is ethacrynic acid.

15. The composition according to claim 12 wherein at least one of said oxidizing agent and said aldehyde or precursor thereof is in the form of a saccharide conjugate.

16. The composition according to claim 12 wherein the oxidizing agent is selected from the group consisting of 4-propoxy phenol, tyrosine, 4-hydroxyanisole, butylated hydroxyanisole, L-3,4-dihydroxyphenylalanine, dopamine, tert-butylcatechol, hydroquinone, resorcinol, 6-hydroxydopa, 4-tert-butyl phenol, 4-tert-amyl phenol, 4-benzomethoxyphenol, and methyl gallate.

17. The composition according to claim 12 wherein the aldehyde or precursor thereof is selected from the group consisting of glyceraldehyde, benzylidene, pyruvaldehyde, mono-, di-, and tri-hydroxy $C_2$–$C_{20}$ straight- and branched-chain aldehydes, citral, and citronal.

18. The composition according to claim 17 wherein the aldehyde or precursor thereof is glyceraldehyde.

19. The composition according to claim 12 wherein the aldehyde or precursor thereof is benzylidene.

20. The composition according to claim 12 wherein the aldehyde or precursor thereof is 4,6,0-benzylidene-D-glucopyranose.

21. The composition according to claim 15 wherein the saccharide is selected from the group consisting of glucuronides, glucose, galactose, fructose, arabinose, mannose, gulose, ribose, xylose, lyxose, erythrose, maltose, cellobiose, lactose, sucrose, N-acetylglucosamine, N-acetylgalactosamine, rhamnose, and mixtures thereof.

* * * * *